(12) United States Patent
Barlov et al.

(10) Patent No.: US 7,959,757 B2
(45) Date of Patent: Jun. 14, 2011

(54) METHOD AND DEVICE FOR MANUFACTURING A MEDICAL LEAD

(75) Inventors: Armin Barlov, Järfälla (SE); Kent Söderman, Vallentuna (SE)

(73) Assignee: St. Jude Medical AB, Jarfalla (SE)

( * ) Notice: Subject to any disclaimer, the term of this patent is extended or adjusted under 35 U.S.C. 154(b) by 170 days.

(21) Appl. No.: 12/281,808

(22) PCT Filed: Mar. 7, 2006

(86) PCT No.: PCT/SE2006/000294
§ 371 (c)(1),
(2), (4) Date: Sep. 5, 2008

(87) PCT Pub. No.: WO2007/102759
PCT Pub. Date: Sep. 13, 2007

(65) Prior Publication Data
US 2009/0025854 A1    Jan. 29, 2009

(51) Int. Cl.
| | |
|---|---|
| B29C 65/00 | (2006.01) |
| B29C 73/00 | (2006.01) |
| B32B 37/00 | (2006.01) |
| B32B 43/00 | (2006.01) |
| B31B 1/60 | (2006.01) |
| A61N 1/00 | (2006.01) |
| A61M 25/00 | (2006.01) |
| A61M 25/16 | (2006.01) |
| A61M 25/18 | (2006.01) |
| A61M 39/00 | (2006.01) |
| A61M 39/10 | (2006.01) |

(52) U.S. Cl. ............ 156/293; 156/60; 156/98; 156/294; 607/122; 607/123; 607/126; 607/128; 607/131; 604/523; 604/524; 604/526; 604/527; 604/528; 604/531; 604/532; 604/533; 604/534; 604/530

(58) Field of Classification Search ............... 156/60, 156/98, 293–294; 264/573; 607/116, 122, 607/123, 126, 128, 131; 604/523, 524, 526–528, 604/530–534
See application file for complete search history.

(56) References Cited

U.S. PATENT DOCUMENTS
2002/0095202 A1 * 7/2002 Schmidt ................. 607/122

FOREIGN PATENT DOCUMENTS
| | | |
|---|---|---|
| GB | 1 427 958 | 3/1976 |
| JP | 2004297979 A * | 10/2004 |
| WO | WO 98/29055 | 7/1998 |
| WO | WO 9829055 A2 * | 7/1998 |

OTHER PUBLICATIONS

Patent Abstracts of Japan, vol. 2003, No. 12, for Japanese Application 2004297979.

* cited by examiner

Primary Examiner — Kat Wyrozebski
Assistant Examiner — Matthew Hoover
(74) Attorney, Agent, or Firm — Schiff Harden LLP

(57) ABSTRACT

In a method and device for mounting an elongated member inside an elongated, elastic, flexible tubing, initially having an inside cross-sectional dimension that is approximately equal to or less than the outside cross-sectional dimension of the elongated member, the inner cross-sectional dimension of the flexible tubing is expanded by applying a pressurized fluid to the inner bore of the tubing, and inserting the elongated member into the tubing while the pressurized fluid is being applied.

5 Claims, 3 Drawing Sheets

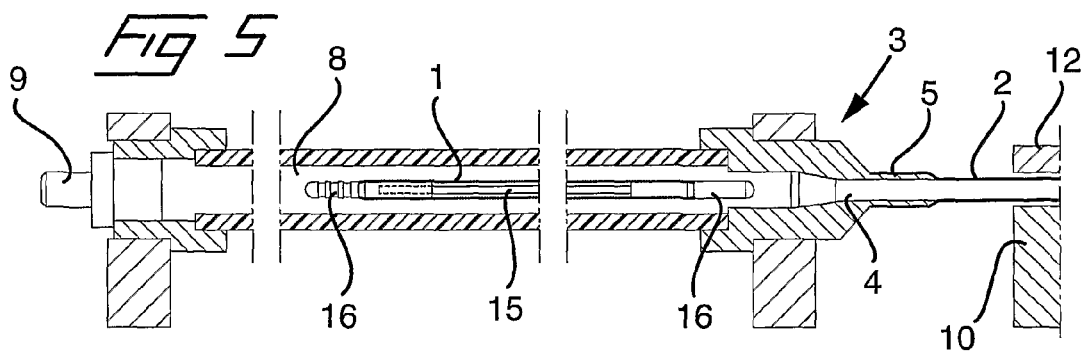
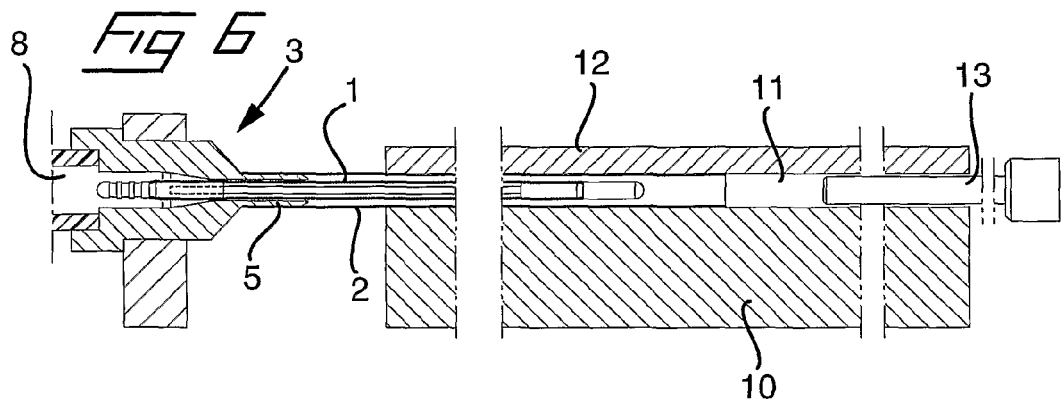
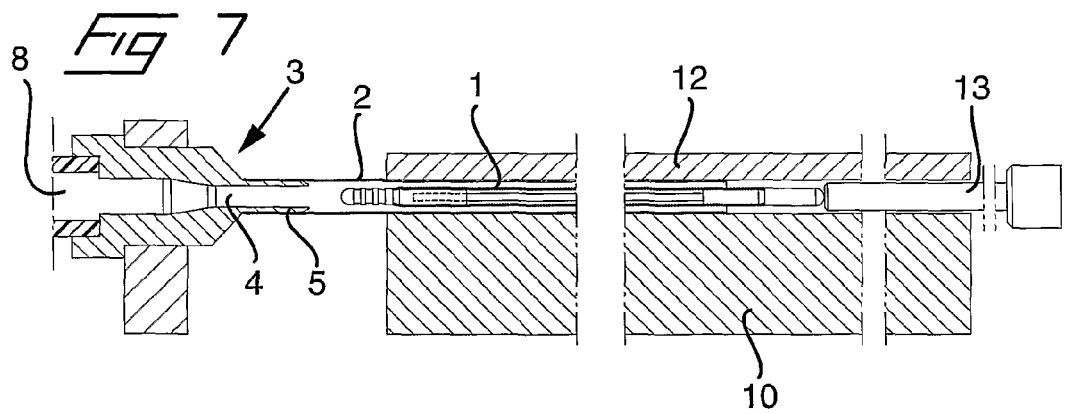
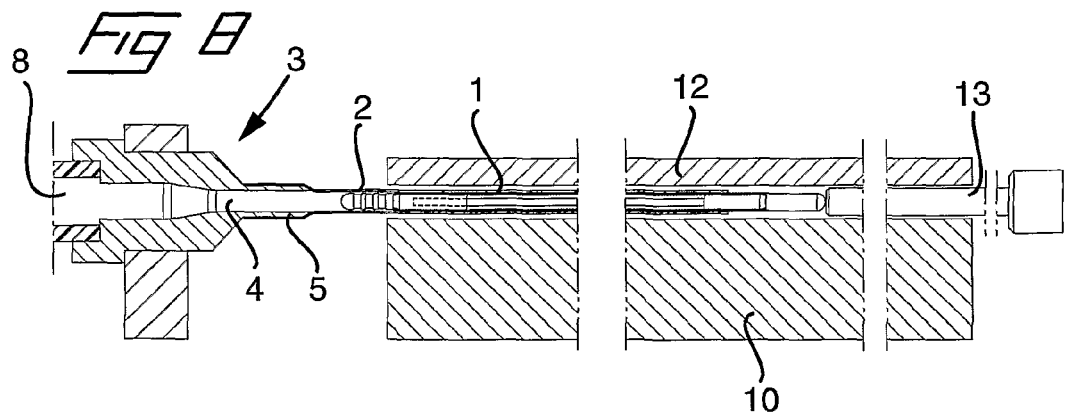

METHOD AND DEVICE FOR MANUFACTURING A MEDICAL LEAD

BACKGROUND OF THE INVENTION

1. Field of the Invention

The present invention relates to a method for mounting of an elongated member inside an elongated, elastic, flexible tubing, initially having an inside cross sectional dimension being about the same size as or smaller than the outside cross sectional dimension of the elongated member.

The invention also relates to a device for performing the mounting.

2. Description of the Prior Art

In different contexts it is desirable to provide an elongated member of some kind, with a shielding layer of an elastic material. This can sometimes be carried out by forming the shielding layer directly onto the elongated member, by for example extrusion. However, in certain cases this kind of operation is not possible to perform for different reasons. Instead the only available option is to insert the elongated member into a flexible tubing of the desired material.

In the field of for example medical implantable leads, it is known to insert or mount an elongated member in form of a metallic coil into a flexible tubing of e.g. silicone. Such leads may preferably be used for pacemaker applications to monitor and pace the activity of a human or animal heart. However, they could also be used for other medical applications, such as for example monitoring, diagnosing or pacing other arbitrary organs inside a body, or for nerve stimulation. The length of such medical implantable leads my vary, but is normally in the range of 40 to 100 cm.

The demands on this kind of medical implantable leads are high. The diameter should be as small as possible, down to about 1 mm in diameter, and they should be highly flexible to be able to be inserted into the body through e.g. narrow blood vessels. When mounting the lead into the body, the lead has to be steerable by means of a steering wire inserted through a bore inside the lead. Moreover, the bore is also utilized when fastening the lead to the desired organ by means of for example a helix in the distal end of the lead, wherein a second, permanently mounted elongated member inside the lead, or a supplementary, temporarily inserted torque transmitting wire is inserted into the bore for performing screw rotation of the helix for screwing it into the tissue and fasten the distal end of the lead to the organ. The coil of the lead should also serve as an electrical conductor for transmitting electrical signals to and from the organ.

The small dimensions as well as the highly flexible characteristics of the coil and the tubing, makes the introducing of the coil into the tubing very difficult. Accordingly, in prior art techniques for performing the assembling, it is known to use different chemical substances, such as for example isopropanol or heptane, serving as a lubricant agent when inserting the coil into the tubing. However, there are some disadvantages associated with this technique. The chemical substances may for instance be unhealthy for the personnel performing the assembling, and they might adversely effect other procedures during the manufacturing, such as gluing. Also, despite the use of lubricating chemical substances, it is still difficult and time consuming to properly insert the coil into the tubing and it is often necessary to use a tubing having an inner cross sectional dimension being larger than desirable to be able to insert the coil into the tubing. This could necessitate the use of an adhesive substance between the coil and the tubing to prevent movement of them in relation to each other during use. It also commonly occurs that the coil will be stretched out or compressed in relation to the tubing during assembling, in which case the assembled coil and tubing has to be relaxed by manually rolling them between hands and a plane surface after assembling.

SUMMARY OF THE INVENTION

An object of the present invention is to eliminate disadvantages associated with prior art methods for inserting of an elongated member into a flexible tubing. More precisely it is an object of the invention to provide a time-saving method, which simplifies the process to mount an elongated member into a flexible tubing.

The invention also relates to a device for mounting of an elongated member into a flexible tubing having essentially the same object as above.

Accordingly, the present invention is based on the use of fluid under pressure to expand or widen the cross sectional dimension of the tubing during insertion of the elongated member into the tubing.

The invention may be implemented in various ways. In a preferred embodiment, the pressurized fluid is air. However, other gases as well as liquids could be used, e.g. water. One advantage with using air, is that it is inexpensive and the assembled tubing and elongated member does not have to be dried after assembling as it normally would when using water or other liquids.

The expansion of the flexible tubing could be performed by a static pressure, if the distal end of the flexible tubing is sealed by any suitable means, such that the flexible tubing is "blown up" similar to a balloon. However, in a preferred embodiment, the expansion is performed by a continuous fluid flow with the distal end of the flexible tubing open. In this way the fluid flow may be used to draw the elongated member into the flexible tubing.

Moreover, the inventive method and device is in a preferred embodiment used for mounting of a metallic coil into a flexible tubing, of for example silicone, for application in a medical implantable lead as mentioned before. However, the method and device could be utilized for other types of applications whenever it is desirable to position an elongated member inside a tight, flexible tubing of an elastic material, when it for some reason is not suitably to form the elastic material directly onto the elongated member by e.g. extrusion.

In a first embodiment of a device for performing the mounting, the device has a nozzle body including an outlet passage and at least one separate, first inlet passage for the fluid and one separate, second inlet passage for the elongated member, with the second inlet passage disposed in alignment with the outlet passage. The outlet is formed as a pipe, on the outside of which the tubing may be threaded with one end. Preferably, the cross sectional dimension of the second inlet passage corresponds closely to the cross sectional dimension of the elongated member, whereas the outlet passage has a somewhat larger cross sectional dimension than the elongated member. In this way the elongated member may be inserted through the second inlet passage and into the outlet passage and when the pressurized fluid flow is turned on, the fluid flow can flow past the elongated member in the outlet passage and into the tubing, which due to the fluid pressure will expand such that the elongated member can be introduced into the tubing without any significant friction between the elongate member and the tubing. Only a small amount of the pressurized fluid will flow out from the second inlet passage since the elongated member has a cross sectional dimension which closely corresponds to the cross sectional dimension of the second inlet passage. Furthermore, since the pressurized fluid is flowing outside of the elongated member in the outlet passage, the fluid flow will help to draw the elongated member into the tubing.

In a second embodiment of the invention, the device also has an elongated pressure chamber in alignment with the outlet passage which is in form of a rigid tube having an inner dimension which is large enough to accommodate the elongated member. The pressure chamber has also an inlet for pressurized air. When mounting an elongated member into a flexible tubing by means of this device, the elongated member is first inserted into the pressure chamber through the outlet passage, thereafter the flexible tubing is threaded onto the pipe of the outlet and finally the pressurized air is turned on. One advantage with this second embodiment in comparison to the first, is that due to the closed pressure chamber, no pressurized fluid will leak in the wrong direction but all of it will pass close to the elongated member into the flexible tubing, such that the elongated member will firmly be drawn into the tubing.

The invention will hereinafter be described specifically in relation to manufacturing of a medical implantable lead for use in pacemaker applications, wherein the elongated member is in form of a coil of a helically formed wire, which is highly flexible and defining an inner bore and which has an outer diameter substantially corresponding to an inner diameter of an elastic, flexible tubing into which the coil will be mounted. However, it should be understood that the inventive method and device, defined by the claims, could be utilized to mount also other types of elongated members into elastic, flexible tubing, e.g. rigid elongated members and/or solid elongated members without any inner bore. It is also possible to utilize the inventive method and device for mounting elongated members having an outer cross sectional dimension being larger than the inner cross sectional dimension of the flexible tubing into which it is to be mounted in.

BRIEF DESCRIPTION OF THE DRAWINGS

FIG. 5 is a cut longitudinal section, in an enlarged scale, showing different portion in the area around the nozzle body of the device of FIG. 4, before the application of pressurized airflow.

FIG. 6 is a cut longitudinal section according to FIGS. 4 and 5, during pressurized airflow.

FIG. 7 is a cut longitudinal section according to FIGS. 4 through 6, during pressurized airflow, when the coil has reached the stop rod.

FIG. 8 is a longitudinal section according to FIGS. 4 through 7, after mounting the coil in the flexible housing when the pressurized airflow is turned off.

DESCRIPTION OF THE PREFERRED EMBODIMENTS

Figure 1:
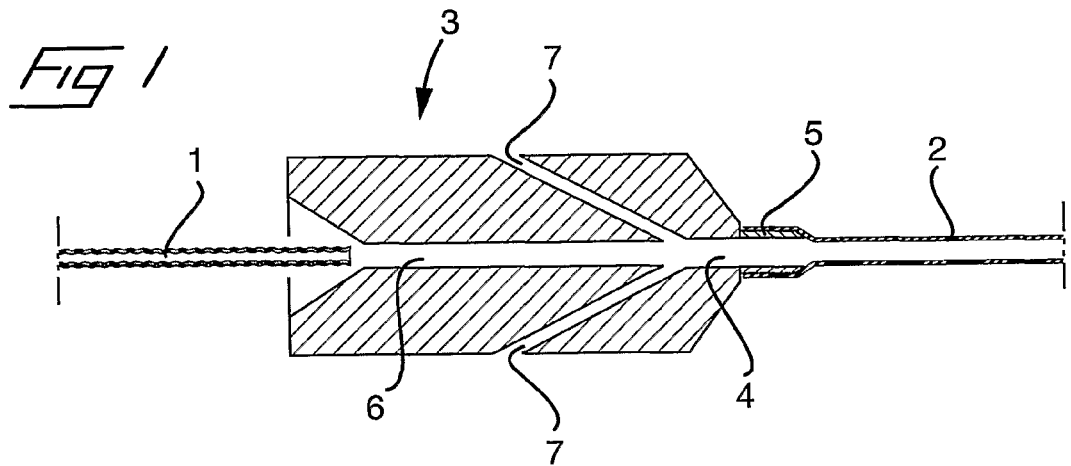
FIG. 1 is a longitudinal section through a schematically illustrated device according to a first embodiment of the invention in a stage before application of pressurized airflow.
Figure 2:
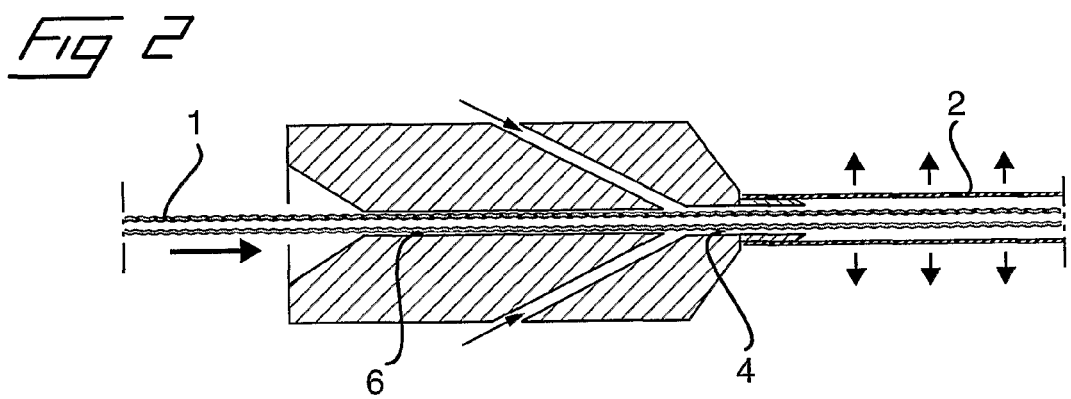
FIG. 2 is a longitudinal section according to FIG. 1 during pressurized airflow, with the coil partly inserted into the flexible tubing.
Figure 3:
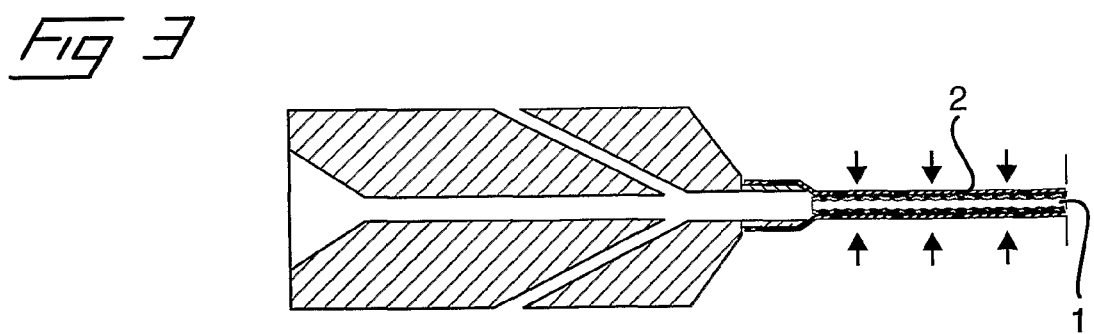
FIG. 3 is a longitudinal section according to FIGS. 1 and 2, with the coil completely inserted into the flexible tubing and the pressurized airflow turned off.

Reference is first made to FIG. 1 to 3 illustrating, in longitudinal sections, a first embodiment of a device for mounting of an elongated member in form of a coil 1 into an elastic, flexible tubing 2. The device comprises a nozzle body generally denoted 3, having an outlet passage 4 forming a pipe 5 in one end of the nozzle body. The outlet passage 4 has a diameter which is slightly larger than the outer diameter of the coil 1. The flexible tubing 2 is with one end threaded onto the pipe 5 and has in an initial, relaxed state an inner diameter which essentially corresponds to the outer diameter of the coil 1. The nozzle body also comprises an inlet passage 6 for the coil 1 which is in alignment with the outlet passage 4. The inner diameter of the inlet passage 6 corresponds closely to the outer diameter of the coil 1. On either side of the nozzle body are formed inlet passages 7 for pressurized air, which are directed in acute angles towards the inlet passage 6 for the coil and converge towards a point where the inlet passage 6 changes into the outlet passage 4. The inlet passages 7 for pressurized air are adapted to be connected to a not shown air pressure source by means of suitably pipes, tubing or the like.

FIG. 1 illustrates a situation where no air pressure is turned on and the coil is outside of the inlet passage 6. In FIG. 2 is illustrated the situation when the pressurized air flow is turned on and the coil 1 is in part inserted through the inlet passage 6, the outlet passage 4 and into the flexible tubing 2. As is shown, the flexible tubing 2 is expanded by the pressurized air, which is flowing between the coil 1 and the inner circumference of the outlet passage 4 due to the larger cross sectional dimension of the latter. The expansion of the tubing enables the coil to slide into the tubing without any significant resistance due to friction against the inner walls of the tubing. The flow rate of the air flow in the direction of the tubing, also helps to draw the coil into the tubing. FIG. 3 illustrates the situation when the coil 1 is completely inserted into the flexible tubing 2 and the pressurized air flow is turned off, such that the flexible tubing is contracted and is pressed toward the coil.

Figure 4:
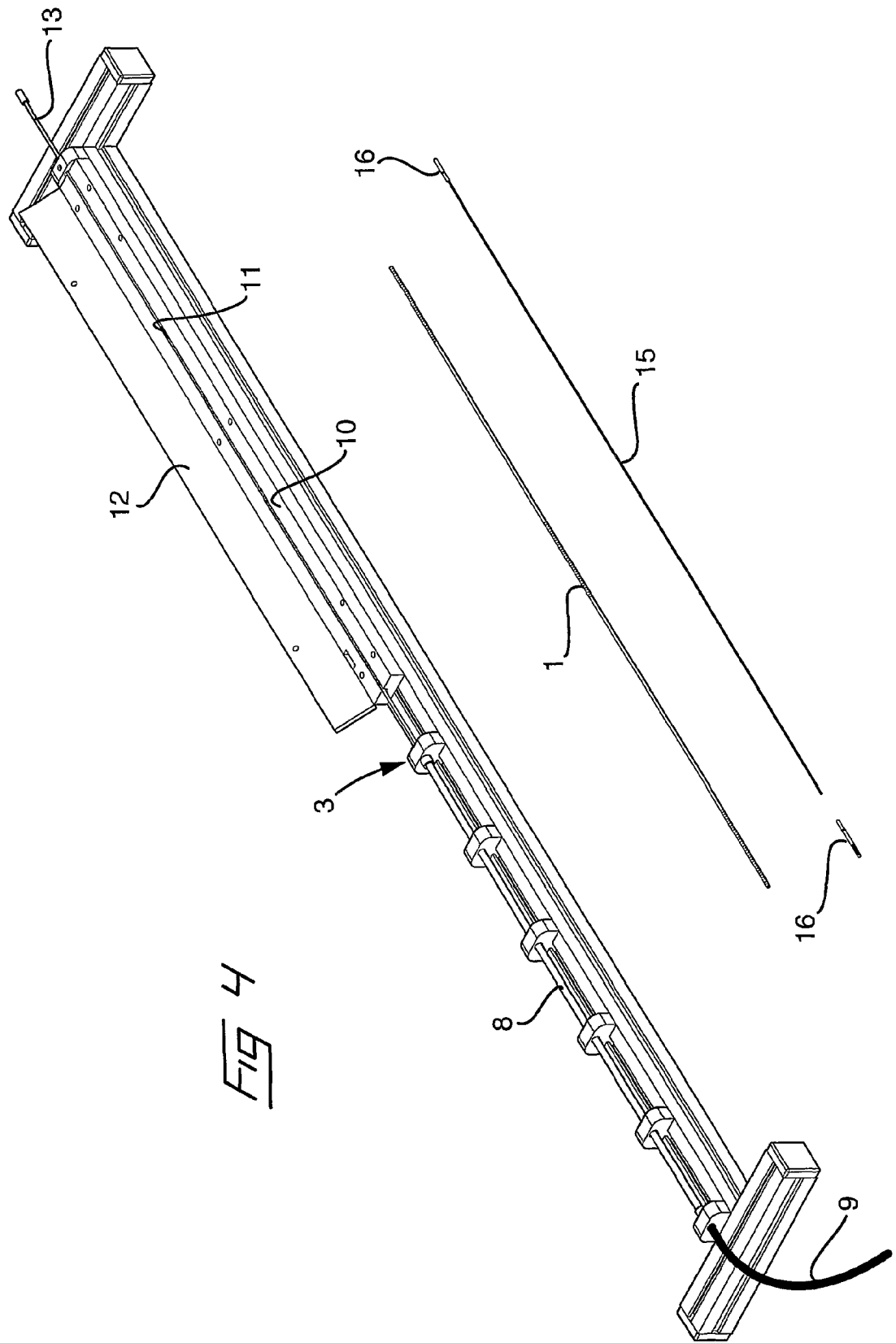
FIG. 4 is a perspective view of a second embodiment of a device according to the invention, with an elongated member in the form of a coil and a reinforcing wire shown separately.

Now reference is made to FIG. 4 of the drawings. Here is shown, in a perspective view, a second embodiment of the invention. As in the previous embodiment, the device comprises a nozzle body 3, having an outlet passage 4 forming a pipe 5 in one end of the nozzle body, as is best seen in FIGS. 5 to 8, which are cut longitudinal sections in an enlarged scale of different portions of the device in the area around the nozzle body. However, instead of separate inlet passages for the coil 1 and the pressurized air, as in the previous embodiment, the device is provided with a pressure chamber 8 in form of a tube, which is in alignment with the outlet passage 4 and which is large enough to accommodate the entire coil 1. In the proximal or forward end of the pressure chamber 8, a conduit 9 for pressurized air is connected. Beyond the nozzle body 3, an elongated box 10 is positioned having a straight groove or slot 11, being in alignment with the outlet passage 4, and a lid 12 which can be closed over the slot 11. In the distal end, the box 10 is provided with a stop rod 13, which with one end extends into the slot 11, having the other end disposed outside of the box and being adjustable in desired positions by means of a set screw.

In FIG. 4 is also shown, separated from the device, a coil 1 and a flexible tubing 2. To reinforce and prevent length deformation of the coil during insertion into the tubing as well as sealing the inner bore of the coil to prevent air flow through the coil during mounting, this embodiment also utilizes a reinforcing wire 15 provided with a stop element 16 in each end of which at least one is detachable.

The procedure to mount the coil 1 into the flexible tubing 2, by means of this second embodiment of the device, is as follows. Firstly the reinforcing wire 15 is inserted into the inner bore of the coil 1 and the stop elements 16 are attached at both ends. The length of the reinforcing wire 15 is adapted to the length of the coil in question, such that the stop elements 16 will be positioned adjacent the ends of the coil. Subsequently the coil 1, including the reinforcing wire 15, is inserted into the pressure chamber 8 through the outlet passage 4 and one end of the flexible tubing 2 is threaded onto the pipe 5. The remaining of the flexible tubing 2 is placed in the slot 11 and the lid 12 is closed. This situation is illustrated in FIG. 8. The coil 1 is now ready for mounting into the flexible tubing and, accordingly, the air pressure is turned on. This will in turn widen the flexible tubing 2 due to the air pressure and the pressurized air flow will draw the coil including the reinforcing wire 15 into the flexible tubing 2, as is illustrated in FIG. 6. The coil will be moved as far into the flexible tubing until the distal stop element 16 of the reinforcing wire 15 hits the end of the stop rod 13, as is shown in FIG. 7. Now the air pressure can be turned off such that the flexible tubing is contracted and is pressed toward the coil, as is illustrated in FIG. 8. Subsequently the lid 12 can be opened and the flexible tubing 2 with the mounted coil 1 be taken away from the device. Finally, the reinforcing wire 15 may be removed from the assembled coil and flexible tubing by detaching at least one of the stop elements 16.

Although modifications and changes may be suggested by those skilled in the art, it is the intention of the inventors to embody within the patent warranted heron all changes and modifications as reasonably and properly come within the scope of their contribution to the art.

We claim as our invention:

1. A method for mounting a tubular elongated member, having an inner bore inside an elongated, elastic flexible tubing, said elastic, flexible tubing initially having an inside cross-sectional dimension that is approximately equal to or less than an outside cross-sectional dimension of the elongated member, comprising the steps of:
   reinforcing and temporarily sealing said inner bore of said elongated member by inserting and advancing a reinforcing member into the inner bore of the elongated member and then temporarily sealing the inner bore with the reinforcing member inserted therein, thereby producing a reinforced elongated member;
   inserting said reinforced elongated member into an elongated pressure chamber having an outlet passage for said reinforced elongated member;
   connecting an inner bore of said flexible tubing with the interior of said pressure chamber through said outlet passage;
   applying pressurized fluid into said elongated pressure chamber so as to obtain a flow of pressurized fluid towards said outlet passage and into said inner bore of said flexible tubing;
   employing said flow of pressurized fluid to expand the inside cross-sectional dimension of the flexible tubing and to draw said reinforced elongated member into said inner bore of said flexible tubing; and
   ceasing application of said pressurized fluid and thereafter breaking the sealing of said inner bore of said elongated member and withdrawing said reinforcing member from said inner bore of said elongated member before completing mounting of said tubular member inside said flexible tubing.

2. A method as claimed in claim 1 comprising employing pressurized air as said pressurized fluid.

3. A method as claimed in claim 1 comprising applying said pressurized fluid continuously to expand said flexible tubing.

4. A method as claimed in claim 3 comprising employing said pressurized fluid flow to insert said reinforced elongated member into said inner bore of said flexible tubing.

5. A method as claimed in claim 1 comprising forming said tubular elongated member as a winding of helically wound wire.

* * * * *